United States Patent [19]
Kritzinger et al.

[11] Patent Number: 5,697,945
[45] Date of Patent: Dec. 16, 1997

[54] CORNEAL SURFACE MARKER AND MARKING METHOD FOR REDUCING IRREGULAR ASTIGMATISM DURING LAMELLAR (LASIK) CORNEAL SURGERY

[75] Inventors: Michiel S. Kritzinger, Westcliff, South Africa; Stephen A. Updegraff, Rapid City, S. Dak.

[73] Assignee: Black Hills Regional Eye Institute, Rapid City, S. Dak.

[21] Appl. No.: 561,541

[22] Filed: Nov. 22, 1995

Related U.S. Application Data

[60] Provisional application No. 60/001,592 Jul. 27, 1995.
[51] Int. Cl.$^6$ ............................................. A61F 9/00
[52] U.S. Cl. .................................. 606/161; 606/166
[58] Field of Search ............................ 606/160, 161, 606/166, 167

[56] References Cited

U.S. PATENT DOCUMENTS

| | | | |
|---|---|---|---|
| 3,818,913 | 6/1974 | Wallach | 128/305 |
| 4,357,941 | 11/1982 | Golubkov et al. | 128/316 |
| 4,406,285 | 9/1983 | Villasenor et al. | 128/305 |
| 4,417,579 | 11/1983 | Soloviev et al. | 128/303 R |
| 4,515,157 | 5/1985 | Fedorov et al. | 128/303 R |
| 4,705,035 | 11/1987 | Givens | 128/303 R |
| 4,739,761 | 4/1988 | Grandon | 606/166 |
| 4,744,360 | 5/1988 | Bath | 128/303.1 |
| 4,963,142 | 10/1990 | Loertscher | 606/14 |
| 5,226,905 | 7/1993 | Hanna | 606/166 |
| 5,250,062 | 10/1993 | Hanna | 606/166 |
| 5,312,330 | 5/1994 | Klopotek | 604/49 |
| 5,314,439 | 5/1994 | Sungita | 606/166 |
| 5,342,378 | 8/1994 | Giraud et al. | 606/166 |
| 5,407,441 | 4/1995 | Greenbaum | 604/280 |
| 5,458,610 | 10/1995 | Feaster | 606/166 |
| 5,549,622 | 8/1996 | Ingram | 606/166 |
| 5,571,124 | 11/1996 | Zelman | 606/166 |

*Primary Examiner*—Michael Buiz
*Assistant Examiner*—Daphna Shai
*Attorney, Agent, or Firm*—Wood,Herron & Evans,L.L.P.

[57] ABSTRACT

A corneal surface marker is used to improve centration and repositioning of a corneal cap or flap in lamellar corneal surgery. The marker has inner and outer concentric rings with marking radial and pararadials extending off the rings to provide adequate reference points for marking indicia to be placed on the corneal surface. The method involves preoperatively marking the corneal surface with suitable indicia in a pattern of radial and pararadial lines extending over the area of the cornea through which an incision will be made to excise a cap or flap and, after the keratotomy is performed, the cap or flap is replaced by realignment of the radial and pararadial lines with the area of the cornea surrounding the incision.

21 Claims, 1 Drawing Sheet

CORNEAL SURFACE MARKER AND MARKING METHOD FOR REDUCING IRREGULAR ASTIGMATISM DURING LAMELLAR (LASIK) CORNEAL SURGERY

RELATED APPLICATIONS

This application is a continuation of Provisional Application Ser. No. 60/001,592, filed Jul. 27, 1995, which is incorporated herein in its entirety by reference. This application is also related to application Ser. Nos. 08/561,744, 08/562,257 and 08/562,253 filed on even date herewith and entitled "Corneal Irrigation Cannula and Method of Using", "Corneal Flap/Cap Elevator" and "Method for Reducing Irregular Astigmatism and Debris/Epithelium in the Interface During Lamellar Corneal Flap/Cap Surgery", respectively, which are incorporated herein in their entireties by reference.

BACKGROUND OF THE INVENTION

Lamellar corneal surgery has undergone a steady evolution over the last 50 years. Advancements in the technology, such as automated keratomes and non-freeze, no-suture techniques have markedly improved safety and effectiveness. During the surface ablation craze of the late 80's, Dr. Gholam Peyman, known for his pioneering retina work, realized the utility of preserving all layers of the cornea but taking advantage of the extreme accuracy of the excimer laser (LASIK). He patented the method for LASIK years ago and studied this technique in his laboratory. He used a YAG laser due to the limited response and acceptance for this technique by the major excimer laser manufacturers. During the years of epikeratoplasty others such as Drs. Lee Nordan and Stephen Slade, as well as Dr. Casimir Swinger were learning and developing freeze myopic keratomileusis for high myopia. By the late 80's, Dr. Slade was one of a hand full of surgeons still performing this demanding technique. When Dr. Luis Ruiz introduced the automated keratome and the in situ non-freeze, no-suture technique to the lamellar bed, Dr. Slade embraced this and has since introduced this technique to thousands of surgeons worldwide. Although a significant advancement, even Dr. Luis Ruiz realized the relative imprecision of making a refractive pass with the keratome. He quickly learned to utilize the excimer laser to precisely reshape the cornea underneath the lamellar corneal flap. The precision achieved has been unparalleled, especially for the moderate to higher myopes.

Worldwide there have been many other surgeons that deserve credit for pursuing the combination of excimer laser with lamellar surgery, most notably Dr. Lucio Buratto of Milan, Italy, and Dr. Ioannis Pallikaris of Greece. The original Buratto technique, however, required cutting a very thick cap and ablating its under surface. Many of these lenticules required suturing, thus required extreme surgical precision and irregular astigmatism rates were quite high. Pallikaris' early work was done on animal models and provided the first histopathology of excimer laser to a lamellar bed. The early Summit excimer laser studies that evaluated the use of lamellar surgery were conducted by Brink et al.; however, there was a significant loss of best corrected visual acuity and a wide range of outcomes as new surgeons attempted to perform the original suture dependent Burrato technique.

As surgeons began doing lamellar surgery, they became concerned about the potential for inducing irregular astigmatism as well as introducing debris such as epithelial inclusions in the interface. Fortunately, with the introduction of the automated keratome and non-freeze, non-suture techniques, irregular astigmatism rates are reduced but still pose a great problem. Debris in the interface also continues to be a chronic problem. Many surgeons have resorted to never wearing gloves during lamellar surgery just for that reason. Although infections in lamellar surgery are quite low, when you are the patient that has the infection, percentages do not matter. At present, it is unclear whether or not wearing gloves during lamellar surgery is the standard of care. Thus, we need a way to perform lamellar surgery with gloves safely so as not to introduce debris into the interface.

There is a growing need to introduce lamellar surgery skills to surgeons new to this arena. Surgeons who have been performing ALK will be prepared to make an easy transition to LASIK. Many of the surgeons making the transition from PRK to LASIK appear totally consumed in what type of ablation to use in the bed, when in reality their primary concerns should be a safe keratectomy and repositioning the cap/flap so that there is the least likely chance for debris in the interface or irregular astigmatism. If that can be reproduced, then enhancement is possible and predictability of the ablation for each surgeon will increase with experience.

Recently a very famous clinical researcher in excimer laser technology expressed that his job is now to make surface ablation PRK as good or better than LASIK. Preserving all the layers of the cornea provides quicker visual recovery and the predictability is less dependent upon the ablation characteristics of the laser. Thus, LASIK in its infancy already has a head start over any surface ablation technique. Secondly, PRK retreatment is unpredictable and problematic while LASIK enhancement is possible and less problematic and destructive. The tremendous amounts of research and development required to create the perfect surface ablation could be better spent in perfecting LASIK for all ranges of refractive errors.

Thus, to improve on techniques in this emerging surgical area, a variety of corneal surface markers which use more precise marking measures for marking the surface of the cornea during surgical procedures have been developed.

U.S. Pat. No. 4,357,941 discloses a tapered instrument for marking out the central optical zone of the cornea during surgical correction of myopia. The instrument has a circular end the diameter of which equals a preset diameter of the central optical zone of a particular patient. Further, a pointed rod-like sight is incorporated into the body of the instrument to aid in alignment. Thus, according to the disclosure, the instrument provides an accurate, clearly outlined central optical zone precluding any possibility of penetration therein when making incisions in the cornea thereby eliminating possible adverse effects. U.S. Pat. No. 4,705,035 also discloses an optical zone marker. This marker has a handle and a collar portion. The collar portion is circular and is adapted to impress an indentation into the cornea with normal hand pressure.

U.S. Pat. No. 4,406,285 discloses a template apparatus for use in manual radial keratotometry. The template is fixed on the eye by suction cups and provides slits to guide the surgical blades when altering the cornea during surgery. As shown in FIGS. 5 through 8, the slits can be in various configurations depending on the particular problem to be corrected.

Both U.S. Pat. No. 4,417,579 and U.S. Pat. No. 4,515,157 disclose corneal incision markers. The markers employ marking edges at one end of a bush which can be aligned in various arrangements. In use, a sufficient amount of force applied by the hand to the devices causes elastic non-destructive deformation of the cornea to mark where the incisions are to be made.

U.S. Pat. No. 4,739,761 discloses a cornea marker that is hand held. The marker has a blade assembly visibly protruding from beneath a radial dial guide allowing rotation of the assembly to selected alignments. The selected alignments aid in correct placement for the particular procedure to be employed.

U.S. Pat. No. 5,226,905 and U.S. Pat. No. 5,250,062 disclose similar instruments for surgery of the cornea. Both instruments are tubular and have annular bottom surfaces which are substantially spherical and are applied to the sclera of the eye of the patient just prior to the surgical procedure. In particular, FIG. 4 of the '905 patent illustrates the design of the annular bottom surface which is concave and has radial ribs for marking the surface of the cornea. U.S. Pat. No. 5,314,439 also describes a tubular element for marking the cornea. The device provides marks on a recipient cornea bed of a corneal transplant patient. The tubular element, which has a spring to retract an inner tube relative to an outer tube, utilizes marking blades spaced circumferentially from each other in various configurations depending on the desired cutout section.

U.S. Pat. No. 5,342,378 discloses a sectioning device for lamellar surgery. FIG. 13 illustrates the marking indicia used in the device. Particular reference is made in the disclosure to an applanator which has these marking indicia on its interior surface. These indicia marked on the interior surface aid in centering the applanator. Furthermore, the use of concentric circles or rings of certain diameters to aid in the centering process is disclosed. According to the disclosure, the inner circle or ring has a diameter that varies from 3.6 mm to 6.5 mm. The outer circle or ring has a diameter of 7.25 min. The crosshair inside the inner concentric ring aid in centering the ring and, in particular, aid in re-centering the ring for the proposed second cut. Indeed, the disclosure states that astigmatism can occur if the inner concentric ring is not centered for the proposed second cut.

Notwithstanding the above and other developments in lamellar or ophthalmologic surgery to date, new and more reliable techniques and instrumentation are needed to positively impact all lamellar surgeons who have grappled with sight-threatening irregular astigmatism and debris in the interface.

SUMMARY OF THE INVENTION

This invention is directed to an improvement in instrumentation and surgical technique for reducing irregular astigmatism and debris/epithelium in the interface during lamellar corneal (lasik) surgery. More particularly, this invention relates to an improved corneal surface marker and marking method for use during lamellar corneal surgery or lasik surgery to improve centration and repositioning of a corneal flap or cap resulting from such surgery.

The corneal surface marker of the present invention comprises a handle for manipulation by hand and a marking surface or device having two concentric rings ensuring centration of the marker and subsequent centration of other instrumentation with the inner ring of the two concentric rings. Marking radials and pararadials extend off of the inner ring and provide adequate reference points for marking indicia on the corneal surface. The radials and pararadials preferably vary in width and extend beyond the concentric rings thereby permitting accurate anatomic repositioning of a free corneal cap or flap while preventing placement of the cap or flap with the epithelial surface down. In other words, the marker and method of using it also prevent the corneal cap from being placed upside down. The inner concentric ring is also preferably provided with a cross-hair to ensure centration of the marker and subsequent centration of other instrumentation.

Furthermore, the inner and outer concentric rings of the marker are circumferentially sized to outline the corneal surface and the optical zone of the corneal surface ensuring accurate centration of the marker for preoperatively marking the corneal surface with suitable indicia. In accordance with these outlines and in its most preferred form, the inner and outer concentric rings of the marker are approximately 5 mm and 10 mm, respectively. Also, the marking radials and pararadials are sufficiently circumferentially spaced around the concentric rings to provide adequate reference points for marking indicia around the area of the corneal surface to be marked. The pararadials include two pararadials extending off the inner concentric ring which are located at the inferior region of the marker. The pararadials are circumferentially spaced 90 degrees apart in this region. They also are of unequal width, one pararadial being at least about twice as wide as the other pararadial permitting accurate anatomic repositioning of a free corneal cap or flap while preventing placement of the cap or flap with the epithelial surface down. The radials located between the nasal, temporal and superior regions of the marker are circumferentially spaced apart equally. The radial positioned superiorly or 90 degrees from the nasal and temporal radials is also at least twice as wide as the other radials positioned in these regions.

The method of marking the corneal surface according to the invention comprises placing the corneal surface marker over the area of the cornea to be marked. The above described marker is then employed for preoperatively marking the corneal surface with suitable indicia, such as pharmacologically acceptable dyes, in accordance with the radials and pararadials of the marker thereby permitting accurate, anatomic repositioning of the free cap or flap. The employment of the radials and pararadials, along with their variance in width enable the accurate anatomic repositioning and prevent the wrong side of the corneal surface (epithelial surface) from being placed onto the corneal bed after the corneal stroma has been surgically reshaped.

These and other advantages of the present invention will become more apparent from the drawings and detailed description.

DETAILED DESCRIPTION OF THE INVENTION

Figure 1:
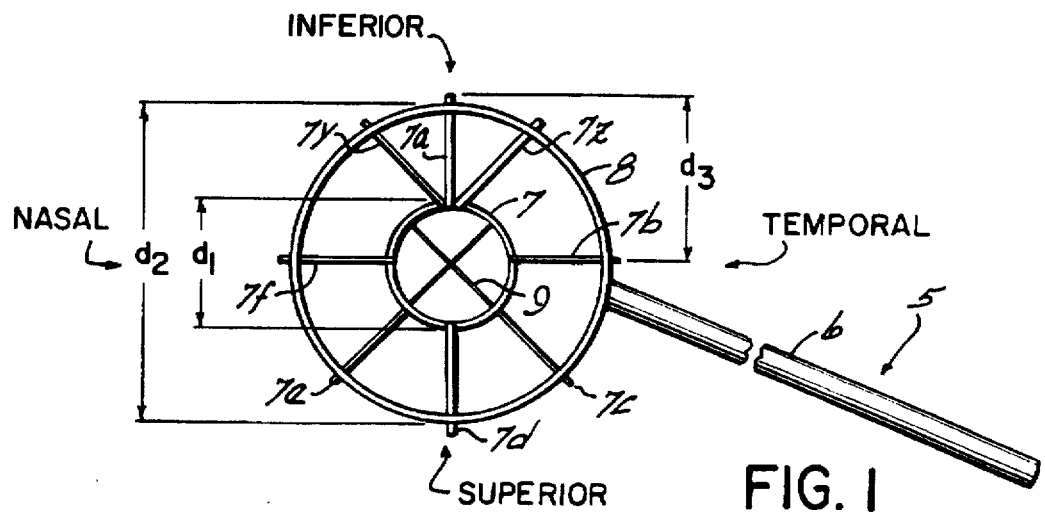
FIG. 1 illustrates a top view of the corneal surface marker of the present invention having a handle and two concentric rings having radial blades with dimensional indications. Also illustrated are the nasal, inferior, temporal and superior regions surrounding the eye over which the surface marker is properly placed prior to marking the corneal surface.

Lamellar corneal surgery has undergone many changes in instrumentation and technique. The most recent advancement is excimer laser in situ keratomileusis or LASIK. This is a non-freeze, non-suture technique that incorporates the precise reshaping of the corneal stroma with the laser and the minimal wound healing/quick recovery of lamellar corneal surgery.

Prior to a lamellar dissection, a corneal surface marker of the present invention is used to outline the anatomical surface of the cornea. Once the lamellar dissection is made and it is appropriate to return the corneal cap/flap, the corneal bed is irrigated with low flow tectonic fluid. The flap/cap is thereby returned. Fluid is aspirated from the fornices such that fluid flows from the bed (top of the dome of the eye) out and downward to the fornices. This first step removes debris and epithelium from the interface. Irrigation should start centrally and move peripherally. The second step requires the suction cannula to be placed gently on the edge of the keratectomy to prevent debris/epithelium from wicking back under the flap/cap. With a layer of irrigation fluid in the interface, the corneal flap/cap is then aligned pursuant to the preoperative surface marking and marking method of the present invention. If debris continues to be present or the cap is not aligned, the method is repeated and the surface markings are realigned.

The present invention and its advantages will be better understood from the following detailed stages of the surgical procedure incorporating references to the accompanying drawing figures. In the various figures, like reference characters are used to designate like parts.

A. Preoperative Stage of LASIK Corneal Surface Marking

1. Eye Prep

We recommend mild lid scrubs to the eyelid margins. Patients diagnosed with meibomianitis or blepharitis should be adequately treated prior to surgery. This may include a short term use of systemic Tetracycline to help reduce meibomian secretions prior to surgery. Be sure to confirm that the patient is not pregnant and is not planning to become pregnant over the next six months as this may affect the outcome of the surgery.

2. Irrigation of the Fornices

A thorough irrigation of the inferior fornices and glove with cool BSS should be conducted. As many have noticed for a long time during cataract surgery when meibomian secretions present as a layer in a pool of irrigating solution, a quick irrigation with the I&A with the head tilted will remove this oily film in a large sheet. This is what we believe is happening when they tilt the patient's head and have already done the lid scrubs and irrigate the fornices. Thus, meibomian secretions are not present during the keratectomy.

3. Eye Drops a. Pilocarpinte 2% is used before the marking ring over the constricted pupil.

b. Light Reflex Constriction

This can be a little more difficult for patients to fixate. It prevents pharmacologic decentration of the pupil and probably is the most accurate way to achieve centration over the entrance pupil.

B. Operative Stage of LASIK Corneal Surface Marking

1. Draping

This is one of the most important steps. Whatever drape you plan to use, it must retract the eyelashes out of the field and the drape should not restrict the speculum from opening fully so that adequate exposure of the globe can be obtained for suction. We presently use a 10–24 drape made by 3M to accomplish this.

2. Irrigation System

At present, we have been using the roller clamp on the IV bottle to control the flow of the BSS Plus through the irrigation cannula. This irrigation system is used to irrigate the globe and cornea prior to surgery.

3. LASIK Corneal Marker and Marking Method

The most recent advancement in corneal surgery is excimer laser in situ keratomileusis or LASIK. This is a non-freeze, non-suture technique that incorporates the precise reshaping of the corneal stroma with the laser and the minimal wound healing/quick recovery of lamellar corneal surgery. A major complication of LASIK corneal surgery which can be sight threatening is irregular astigmatism. To date, corneal surgeons have used subtle and often imperceptible visual cues to reapproximate the flap or corneal tissue. It is apparent that a slight decentration or disorientation of the flap can result in irregular astigmatism.

Thus, with the above preoperative surgical procedures detailed and the dramatic problems of imprecise results of corneal surgery outlined, we propose an embodiment of a corneal surface marker of the present invention shown generally at 5 in FIG. 1 of the drawings. The corneal surface marker 5 improves centration of the surgical procedure and apparatus and precisely repositions the corneal cap or flap 3c after the ablation stage of the surgical procedure.

Figure 2:
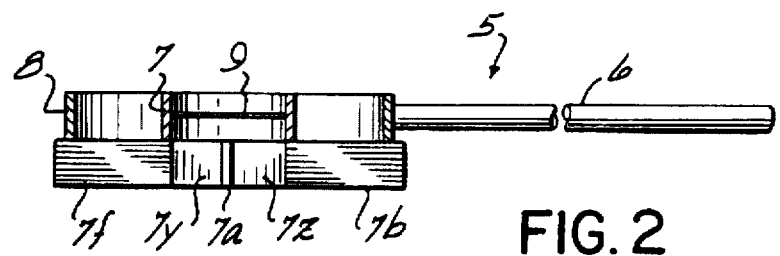
FIG. 2 is a cross-sectional side view of FIG. 1.

In its most preferred embodiment, the Kritzinger-Updegraff (KU) LASIK marker 5 of FIG. 1 consists of a handle 6 and two concentric rings, 7 and 8; ring 7 being 5 mm in diameter $d_1$ with crosshair 9 (to aid centering) and ring 8 being 10 mm to 10.5 mm in diameter $d_2$. The rings 7 and 8 of FIG. 1 may be formed of metal with radial blades 7a–7f and pararadial blades 7y–7z extending therefrom, as also shown in FIG. 2 cross-sectional side view. The diameters of the rings are important in that they approximate the specific areas of the cornea to be covered and eventually worked. Further, radiating off the center ring 7 are six radials, shown in the figures as 7a, 7b, 7c, 7d, 7e, 7f, and two pararadials, shown as 7y and 7z, which extend approximately 6 mm from the center of the crosshair 9 or at any length $d_3$ sufficient to cross and give adequate reference points past ring 8. These radial and pararadial markers vary in width as shown in FIG. 1 which permits precise repositioning of the cap or flap edges after the keratectomy and ablation have been performed. Further, as shown in FIG. 1, marker 5 is properly placed over the eye in the position indicated and outlined by the surrounding regions of the eye. These regions are the nasal, temporal, inferior and superior. The width of the superior radial 7d and inferior radial 7a as well as the temporal pararadial 7z are at least two times thicker than the other radials 7b, 7c, 7e, 7f and pararadial 7y. The pararadials 7y and 7z at 11:00 and 1:00 are of different width and converge upon radial 7a at an angle within the outer concentric ring 8 to ensure proper orientation of a free cap and prevent placement of a free cap upside down (epithelial surface down). The marker 5 was developed to permit a centered keratectomy which is dependent upon outer ring 8 on which the surgeon centers a suction ring before the surgical incision is made. Additionally, the concentric rings 7 and 8 ensure centration of the mark and subsequent centration of the LASIK suction ring or other appropriate instrumentation during the course of the surgical steps. The different widths of the pararadials and radials permit accurate, anatomic repositioning of the cap or flap after ablation microsurgery of the cornea is complete. The radial and pararadial markings also provide adequate reference points with the large flaps made with the LASIK suction ring.

Figures 3A, 3B:
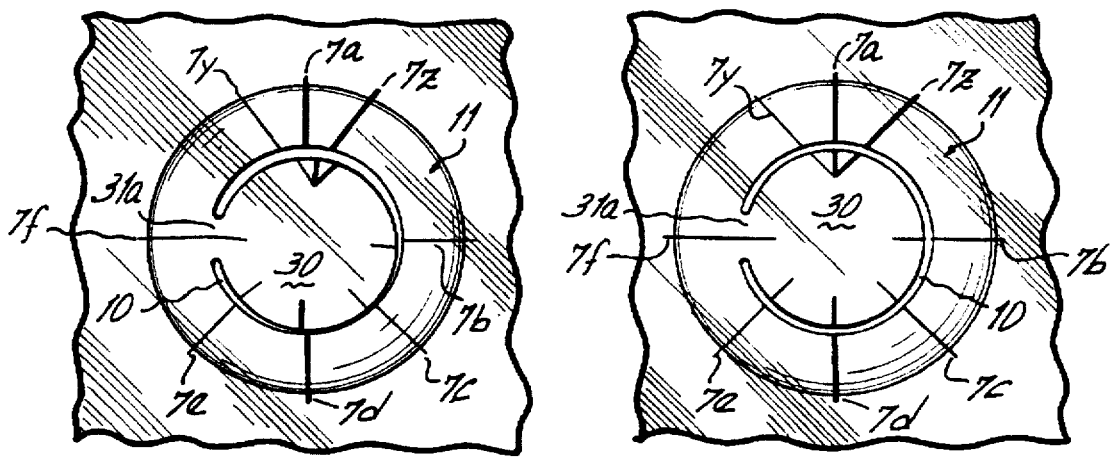
FIG. 3A is an illustration of a misaligned corneal cap post surgical procedure whereby the radial and pararadial marks directed by the present invention indicate the incorrect positioning of the corneal cap.
FIG. 3B is an illustration of a correctly aligned corneal cap post surgical procedure whereby the radial and pararadial marks directed by the present invention indicate the correct, accurate and precise anatomical repositioning of the corneal cap.

As shown in FIGS. 3A–3B, the radiating marks extend beyond the incision ring created by the keratectomy and prevent micro-decentration seen when the surgeon uses an equally gapped gutter 10 in the cornea 11 as the cue for alignment. This latter imprecise method of alignment is thus rendered unnecessary.

When the marker 5 described in detail above is used with a marking dye and properly placed in position over the corneal surface as illustrated in FIG. 1, and the marking radials and pararadials are aligned correctly, the pharmacologically safe dye is preoperatively placed as indicia on the corneal surface in the pattern outlined by the marker 5 so that the keratectomy and stromal reshaping by the surgeon may begin. Thereafter, the radial and pararadial markings are then aligned so that the free corneal cap or flap is accurately, anatomically positioned thereby reducing the possibility of a post surgical procedure for astigmatism. The correct anatomical alignment is illustrated in FIG. 3B of the drawings.

4. Laser Centration a. Positioning the Patient's Head

The goal is to have the globe absolutely centered in the patient's socket as the patient fixates on the red fixation beam of the excimer laser device. An attempt should be made to position the patient's chin and forehead so that the globe is on a flat plane. It is important to make sure that the chin cannot move up or down and the head must be stable so that it cannot turn left or right. Once you have the globe centered within the orbit and looking straight ahead, use the joy stick of the X axis to bring the patient "dead" center in the crosshair that is in the optics of the right eye piece.

The KU marker 5 is then positioned so that the superior and medial lateral marks of the crosshair of the eyepiece match with those of the marker ring 7. Thus, after creating the mark, the crosshairs can be superimposed upon it. If there is not absolute correspondence of the crosshair in the mark that is placed on the cornea, the surgeon is then responsible to make a "mental note" of this orientation when ablating the stromal bed and putting the flap back into position pursuant to the preoperative markings as outlined in the previous stage.

At this point with the Keracor 116 laser, the red and green light must be superimposed prior to placing these marks or the crosshair will move away from the center of the pupil after these maneuvers have been performed.

b. Applying the Suction Ring

It is important to have the circular rings 7 and 8 of the KU marker 5 aligned concentrically with the suction ring. This ensures that the flap will properly be central to the pupil or the central optical zone.

c. Ablation

After the keratectomy is performed, the flap or cap is folded back toward the nasal region. The peripheral markings of the KU marker are still visible. Thus, these are used as a visual cue to line up the cross-hair of the redicule which correspond to the exact fixation prior to the keratectomy. It is very important not to move the joy stick of the excimer laser at this point to center the ablation. Rather, move the patient's head gently to achieve centration. Improper alignment of the patient's head does not mean the bed has moved but rather the patient's head has moved and thus must be oriented back to the position you had initially worked so hard to achieve. Thus, it is imperative that the joystick of the excimer laser is not altered from its original position.

It should be understood that the embodiments of the present invention shown and described in the specification are only preferred embodiments of the inventors who are skilled in the art and are not limiting in any way. Therefore, various changes, modifications or alterations to these embodiments may be made or resorted to without departing from the spirit of the invention and the scope of the following claims.

We claim:

1. A corneal surface marker to improve centration and repositioning of a corneal cop or flap in lamellar corneal surgery comprising inner and outer concentric rings ensuring centration of said marker, a marking radial and pararadial extending off said rings thereby providing adequate reference points for marking indicia on the corneal surface, said marking radial and pararadial converging upon each other at an angle within said outer concentric ring thereby permitting accurate anatomic repositioning of a free corneal cap or flap.

2. The corneal surface marker of claim 1 having a handle for manipulation of said marker.

3. The corneal surface marker of claim 1 sized to be placed over the human eye for centration of the marking indicia and surgical instrumentation.

4. The corneal surface marker of claim 3 wherein said inner concentric ring has a crosshair in its interior for accurate centration over the eye.

5. The corneal surface marker of claim 1 wherein at least one of said marking radial and pararadial varies in width permitting accurate anatomic repositioning of a free corneal cap or flap.

6. A corneal surface marker to improve centration and repositioning of a corneal cap or flap in lamellar corneal surgery comprising:

a handle for manipulation, and a marking surface, said marking surface having two concentric rings ensuring centration of said marker and subsequent centration of other instrumentation with the inner ring of said concentric rings having a cross-hair in its interior and marking radials and pararadials extending off said inner ring providing adequate reference points for marking indicia on the corneal surface, said radials and pararadials varying in width and extending beyond the outer concentric ring thereby permitting accurate anatomic repositioning of a free corneal cap or flap while preventing placement of said cap or flap with the epithelial surface down.

7. The corneal surface marker of claim 6 wherein said inner and outer concentric rings are circumferentially sized to outline the corneal surface and the optical zone of said corneal surface ensuring accurate centration of said marker for marking the corneal surface with suitable indicia.

8. The corneal surface marker of claim 7 wherein said inner and outer concentric rings are approximately 5 mm and 10 mm, respectively.

9. The corneal surface marker of claim 6 wherein said marking radials and pararadials are sufficiently circumferentially spaced around said concentric rings to provide adequate reference points for the marking indicia and the area of the corneal surface to be marked.

10. The corneal surface marker of claim 6 wherein said pararadials include two pararadials extending off said inner concentric ring from a common point at a 90° angle with respect to each other.

11. The corneal surface marker of claim 10 wherein said two pararadials are of unequal width, one pararadial being at least about twice as wide as the other pararadial permitting accurate anatomic repositioning of a free corneal cap or flap.

12. The corneal surface marker of claim 6 having a plurality of radials and at least one pararadial.

13. The corneal surface marker of claim 12 having two pararadials.

14. A method of marking the corneal surface during corneal surgery for repositioning a corneal cap or flap comprising:

preoperatively marking the corneal surface with suitable indicia in a pattern of radial and pararadial lines extending over the area of the cornea through which an incision will be made to excise a cap or flap, at least one radial line and at least one pararadial line converging upon each other at an angle within said area, circumferentially incising said corneal surface across said radial and pararadial lines to form said cap or flap, removing said cap or flap from said surface having said radial and pararadial lines remaining on the cap or flap and the corneal surface beyond said circumferential incision for postoperative realignment, and realigning said remaining radial and pararadial lines of said cap or flap with those on the corneal surface beyond said circumferential incision.

15. A method of marking the corneal surface comprising:

placing a corneal surface marker over the area of the cornea to be marked, said marker having two concentric rings ensuring centration of said marker, a marking radial and pararadial extending off said rings thereby providing adequate reference points for the marking indicia to be placed on the corneal surface, said radial and pararadial varying in width, preoperatively marking the corneal surface with suitable indicia in accordance with the radial and pararadial of said marker thereby permitting accurate anatomic repositioning of a free corneal cap or flap while preventing placement of said cap or flap with epithelial surface down onto said corneal bed after surgical reshaping of the corneal stroma.

16. A method of marking the corneal surface according to claim 15 wherein said suitable indicia used for preoperatively marking the corneal surface is a pharmacologically safe dye.

17. A method of marking the corneal surface according to claim 15 by marking with the radial and pararadial extending beyond the outer concentric ring and varying in width thereby permitting accurate anatomic repositioning of a free corneal cap or flap.

18. A method of marking the corneal surface according to claim 15 by marking with said inner and outer concentric rings of approximately 5 mm and 10 mm, respectively.

19. A method of marking the corneal surface according to claim 15 by marking radials and pararadials sufficiently circumferentially spaced around said concentric rings to provide adequate reference points for the marking indicia and the area of the corneal surface to be marked.

20. A method of marking the corneal surface according to claim 15 marking with two pararadials extending off said inner concentric ring from a common point at a 90° angle with respect to each other.

21. A method of marking the corneal surface according to claim 15 by marking two pararadials of unequal width, one pararadial being at least about twice as wide as the other pararadial thereby permitting accurate anatomic repositioning of a free corneal cap or flap.

* * * * *